United States Patent [19]

Akiba et al.

[11] Patent Number: 4,892,816

[45] Date of Patent: Jan. 9, 1990

[54] METHOD FOR THE DETERMINATION OF CHOLESTEROL

[75] Inventors: Tetsunori Akiba, Kani; Kuniyoshi Matsunaga, Ichinomiya, both of Japan

[73] Assignee: Amano Pharmaceutical Co., Ltd., Aichi, Japan

[21] Appl. No.: 136,522

[22] Filed: Dec. 22, 1987

Related U.S. Application Data

[63] Continuation of Ser. No. 788,581, Oct. 17, 1985, abandoned.

[30] Foreign Application Priority Data

Oct. 31, 1984 [JP] Japan ................. 59-229290

[51] Int. Cl.$^4$ .............. C12Q 1/60; C12Q 1/44; C12Q 1/26; C12Q 1/32
[52] U.S. Cl. .................... 435/11; 435/19; 435/25; 435/26; 435/810
[58] Field of Search .......... 435/11, 19, 26, 188, 435/810, 25

[56] References Cited

U.S. PATENT DOCUMENTS

| | | | |
|---|---|---|---|
| 4,164,448 | 8/1979 | Roeschlau et al. | 435/11 |
| 4,181,575 | 1/1980 | Gruber et al. | 435/11 |
| 4,294,923 | 10/1981 | Smith et al. | 435/23 |
| 4,457,916 | 7/1984 | Hayashi et al. | 424/101 |

FOREIGN PATENT DOCUMENTS

| | | | |
|---|---|---|---|
| 0067394 | 12/1982 | European Pat. Off. | 435/11 |
| 89200 | 5/1983 | Japan | 435/11 |
| 210000 | 12/1983 | Japan . | |
| 1412244 | 10/1975 | United Kingdom . | |

OTHER PUBLICATIONS

Flegg, H. M., Ann. Clin. Biochem., 10 (1973), 79.
The Merk Index, 1983, 10th edition, Merk and Co. Inc., Rahway, N.J., p. 6603.
Derwent Publications Ltd., (Jul. 12, 1983), item number C84–008427.
Allain et al., *Clinical Chemistry*, vol. 20, No. 4, pp. 470–475 (1974).

*Primary Examiner*—Esther M. Kepplinger
*Attorney, Agent, or Firm*—Wegner & Bretschneider

[57] ABSTRACT

An enzymatic method for measurement of cholesterol comprises incubating:
(a) a test sample;
(b) a cholesterol dehydrogenase;
(c) an oxidizing agent selected from the group consisting of nicotinamide - adenine dinucleotide (NAD) and nicotinamide - adenine dinucleotide phosphate (NADP); and
(d) a surfactant
and measuring the resulting detectable oxidized and reduced products kinetically.

A composition for the kinetic measurement of cholesterol comprises:
(a) a cholesterol dehydrogenase;
(b) an oxidizing agent selected from the group consisting of nicotinamide - adenine dinucleotide (NAD) and nicotinamide - adenine dinucleotide phosphate (NADP); and
(c) a surfactant.

13 Claims, 3 Drawing Sheets

METHOD FOR THE DETERMINATION OF CHOLESTEROL

This application is a continuation of U.S. application Ser. No. 788,581, filed Oct. 17, 1985, now abandoned.

BACKGROUND OF THE INVENTION

1. Field of the Invention

This invention relates to a method for the kinetic determination of cholesterol using a cholesterol dehydrogenase as well as to a reagent composition therefor. More particularly, the present invention relates to a method for the determination of cholesterol which comprises incubating a sample, a cholesterol dehydrogenase, and nicotinamide-adenine dinucleotide (after referred to as NAD) or nicotinamide-adenine dinucleotide phosphate (after referred to as NADP) in the presence of from about 10 to about 100 mg/ml of a surfactant and then measuring the resulting detectable change kinetically, as well as to a reagent composition therefor.

2. Description of the Prior Art

As enzymatic methods for the determination of cholesterol, there are known methods wherein free cholesterol and esterified cholesterol are subjected to chemical or enzymatic saponification to convert the latter cholesterol to free cholesterol. All the free cholesterols are allowed to react with a cholesterol oxidase, and the formed hydrogen peroxide or cholestenone or the consumed oxygen is measured (Clin. Chem., 20, 470, 1974; U.S. Pat. Nos. 3,925,164 and 4,212,938 and GB Pat. No. 1,412,244). The most widely used of these methods using a cholesterol oxidase is a method wherein the formed hydrogen peroxide is allowed to react with a peroxidase and a color-producing reagent and the resulting colored substance is measured. However, this method has drawbacks in that a reagent of intricate composition needs to be used and the measurement is affected by bilirubin and ascorbic acid both present in blood together with cholesterol causing a measurement error.

There are also known methods wherein, in place of the cholesterol oxidase used above, a cholesterol dehydrogenase and NAD or NADP as a connzyme are used and the formed cholestenone or the reduced type NAD (after referred to as NADH) or reduced type NADP (after referred to as NADPH) formed is measured (U.S. Pat. No. 4,181,575; FRG Patent Laid-open No. 3,032,377 and Japanese Patent Laid-open No. 89,200/1983). Of these methods using a cholesterol dehydrogenase, the method of measuring the formed NADH or NADPH is advantageous in that the measurement is not affected by the above mentioned hindering substances present in blood together with cholesterol.

These conventional methods for the determination of cholesterol using a cholesterol oxidase or a cholesterol dehydrogenase are so-called end point assay methods and, in these methods, cholesterol as a substrate must be allowed to react until it is completely converted to a reaction product. Therefore, there has generally been employed a measurement time of 5 to 10 min, a blank test for each sample and a relatively large amount of an enzyme. In recent years, in the field of clinical chemical inspection, measuring a large number of samples in a short time and with accuracy has been required which has led to the development of automatic analytical equipment and apparatuses. In measurements by automatic analytical equipment and apparatuses, the measurement time is required to be as short as possible. Hence, in place of the end point assay methods, there were proposed methods wherein the initial rate of reaction is measured, namely, kinetic measurement methods called "rate assay". In the study on method for the determination of the cholesterol, too, there was tried a kinetic measurement method using a cholesterol oxidase. However, the reaction did not proceed according to the first order or pseudo-first order because the Km (Michaelis's constant) value of the enzyme was too low compared with 500.0 mg/dl or more of cholesterol (this is a level necessary for determination of cholesterol). It is reported that, in order to artificially increase this unacceptably low Km value, a method of adding 3,4-dichlorophenol was tried and, as a result, the Km value of cholesterol oxidase was increased and kinetic measurement of cholesterol has been made possible (European Pat. No. 53,692). However, this method of using a cholesterol oxidase is not free from the above mentioned interference by hindering substances present in blood.

SUMMARY OF THE INVENTION

According to one aspect of the present invention, there is provided an enzymatic method for the determination of cholesterol, wherein a test sample, a cholesterol dehydrogenase, and an oxidizing agent selected from the group consisting of NAD or NADP are incubated in the presence of from about 10 to about 100 mg/ml of a surfactant and the resulting detectable oxidized and reduced products are measured kinetically.

According to another aspect of the present invention, there is provided a reagent composition for the kinetic determination of cholesterol, comprising a cholesterol dehydrogenase, an oxidizing agent selected from the group consisting of NAD or NADP, and from about 10 to about 100 mg/ml of a surfactant.

DETAILED EXPLANATION OF PREFERRED EMBODIMENTS OF THE INVENTION

Figure 1:
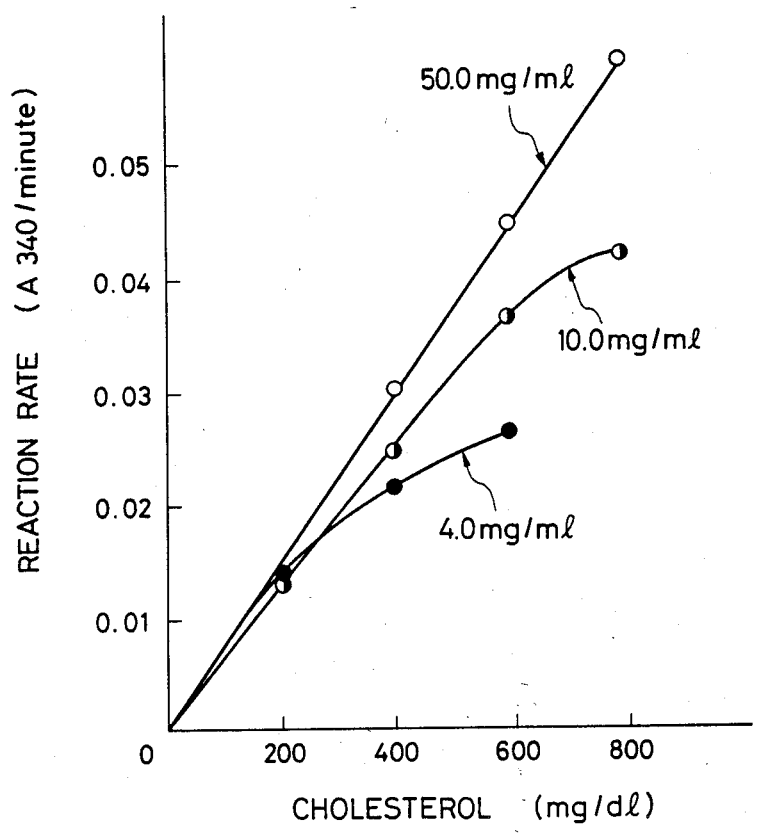
FIG. 1 illustrates the effect of the addition of a surfactant (Triton X-100) on the relation between cholesterol concentration in sample and reaction rate of cholesterol dehydrogenase, in accordance with the method for the determination of cholesterol according to the present invention.

According to the present invention, there are provided a method for the kinetic determination of cholesterol using a cholesterol dehydrogenase and a reagent composition therefor.

The cholesterol dehydrogenase used in the present invention catalyzes a reaction of converting cholesterol to cholestenone in the presence of NAD or NADP as a coenzyme and concurrently converting the coenzyme of oxidizing type to a coenzyme of reducing type, as shown in the following formula.

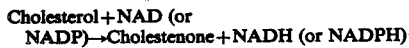

Cholesterol+NAD (or NADP)→Cholestenone+NADH (or NADPH)

Examples of the cholesterol dehydrogenase preferably used in the present invention are disclosed by one of the present inventors in Japanese Patent Laid-open Nos. 89,183/1983 and 89,200/1983 concerned with the preparation of cholesterol dehydrogenase, its properties and the determination of cholesterol using the enzyme in accordance with the end point assay method. That is, there are mentioned in the above publications cholesterol dehydrogenases produced by Nocardia sp No. Ch 2-1 (FERM-P No. 6,217), Alcaligenes sp No. 4 (FERM-P No. 6,216), and Proteus vulgaris (IAM 1,025). All these cholesterol dehydrogenases, having too low Km values of an order of $10^{-4}$ M, cannot be used, as they are, for the kinetic determination of cholesterol. According to the theory of Michaelis-Menten, when a substrate concentration is sufficiently low compared with the Km value of an enzyme, the rate of this enzymatic reaction is proportional to the substrate concentration and accordingly the kinetic determination of the substrate concentration is possible. According to the present invention, use of a reaction solution containing from about 10 to about 100 mg/ml of a surfactant has sufficiently increased the Km value of cholesterol dehydrogenase, whereby the kinetic determination of cholesterol has been achieved.

It has been known that, in the field of clinical chemical analysis, surfactants are used for purposes such as solubilization or emulsification of substrate, stabilization or activation of reagent, and the like. For example, in the above mentioned determination of cholesterol using a cholesterol dehydrogenase according to the end point assay method, developed by the present inventors, 2.7 mg/ml of Triton X-100 is added to activate the enzyme and to solubilize a substrate. Also in the kinetic measurement of cholesterol using a cholesterol oxidase of European Pat. No. 53,692, 1 to 10 mg/ml of a non-ionic surfactant and 0 to 15 mmol/l of a surfactant of cholic acid group (0 to 6.5 mg/ml as sodium cholate) are added although this is not intended to increase the Km value of the enzyme. The concentration of these surfactants added for the above purposes is generally about 10 mg/ml or less and a concentration higher than this is undesirable. According to the present invention, the kinetic determination of cholesterol has been achieved by using a surfactant in a concentration far higher than that conventionally used.

The present invention provides a method for the kinetic determination of cholesterol using a cholesterol dehydrogenase and a reagent composition therefor. According to the present invention, the kinetic determination of cholesterol has been achieved by simply adding from about 10 to about 100 mg/ml of a surfactant to a reaction solution and add as a result shortening the measurement time, eliminating the blank test, and significantly saving of amount the cholesterol dehydrogenase used.

The surfactant advantageously used in the composition and the method of the present invention, is preferably a non-ionic surfactant of polyoxyethylene alkylphenol ether type, polyoxyethylene alkyl ether type, secondary straight alcohol ethoxylate type, or nonylphenol ethoxylate type having a HLB of 8 to 20. Specific examples of these preferable surfactants include polyoxyethylene alkylphenol ether type polyoxyethylene (9,10) p-t-octylphenyl ether [Triton X-100 (trade name) manufactured by Katayama Chemical Industries Co., Ltd.], polyoxyethylene (8 to 85) p-nonylphenyl ether [Emulgen 903 (trade name) manufactured by Kao-Atlas Chemicals], the non-ionic surfactants of polyoxyethylene alkyl ether type polyoxyethylene (20) cetyl ether [Brij 58 (trade name) manufactured by Kao-Atlas Chemicals], polyoxyethylene (10) cetyl ether [Brij 56 (trade name) manufactured by Kao-Atlas Chemicals], polyoxyethylene (23) dodecyl ether [Brij 35 (trade name) manufactured by Kao-Atlas Chemicals], polyoxyethylene (10) lauryl ether (manufactured by Sigma Co.), polyoxyethylene (14) stearyl ether [Emulgen 320P (trade name) manufactured by Kao-Atlas Chemicals], polyoxyethylene (10) oleyl ether [Brij 96 (trade name) manufactured by Kao-Atlas Chemicals], polyoxyethylene (29) oleyl ether [Brij 98 (trade name) manufactured by Kao-Atlas Chemicals], the surfactants of secondary straight alcohol ethoxylates [Adekatol S080, Adekatol S0135 and Adekatol LG295-S (trade names) manufactured by ASAHI Electro-Chemical Co., Ltd.] and the surfactants of nonylphenol ethoxylates [Adekatol NP 1100 and Adekatol NP-700 (trade names) manufactured by ASAHI Electro-Chemical Co., Ltd.]. These non-ionic surfactants may also be used in combination with other surfactants such as, sodium cholate.

The concentration of surfactant to be added is preferably from about 10 to about 100 mg/ml. When the concentration is less than 10 mg/ml, the Km value of cholesterol dehydrogenase is not sufficiently increased, whereby the range of substrate concentration which can be measured is narrowed. When the concentration exceeds 100 mg/ml, the viscosity of reaction solution increases and the activity of enzyme is impaired, both of which are undesirable.

According to the present invention, a test sample, such as human body fluid, a cholesterol dehydrogenase, and NAD or NADP are incubated in the presence of the above mentioned surfactants and the resulting detectable change is measured kinetically, whereby free cholesterol can be determined. When in the above incubation, a cholesterol esterase is used in addition to the cholesterol dehydrogenase, both of free cholesterol and bound (esterified) cholesterol can be determined. The reaction solution may further contain a substance which reacts with the formed NADH or NADPH to produce a colored compound, a buffer solution, and a stabilizer for enzyme.

In the present invention, detectable change taking place in the reaction can be measured in accordance with any appropriate method. Cholesterol can be determined by measuring the formed cholestenone or the formed reduced products NADH or NADPH. The formed oxidized product cholestenone can be measured by measuring the absorption at 240 nm of the reaction solution itself using a photometer. The formed reduced products NADH or NADPH can be measured by measuring their fluorescence intensity. Preferably, the formed NADH or NADPH can be measured by (a) a method wherein the absorption at 340 nm of the reaction solution itself is measured using a photometer, or by (b) a method wherein the hydrogen of the formed reduced products NADH or NADPH is transferred to tetrazolium salt via an electron transferring agent such as diaphorase, phenazine methosulfate or the like and the resulting formazan is subjected to measurement of absorption at visible region using a photometer. As the preferable tetrazolium salt, there can be mentioned Indonitrotetrazolium Violet (INT) and Nitrotetrazolium Blue (NTB). The latter method (b) of measuring a colored substance formed has an advantage in that the amount of surfactant used in the reaction of the present invention can be reduced.

The temperature and pH used in the reaction of the present invention is not critical as long as a sufficient enzymatic activity is kept. Preferably, the temperature is from about 20° to about 40° C. and the pH is from about 6 to about 10.

Another object of the present invention is to provide a reagent composition usable in the kinetic determination of cholesterol. This reagent composition comprises at least a cholesterol dehydrogenase, NAD or NADP, and from about 10 to about 100 mg/ml (in final working solution) of a surfactant. The reagent composition can optionally comprise, as already mentioned, a cholesterol esterase, tetrazolium salt, an electron transferring agent such as diaphorase or the like, a buffer solution, and a stabilizer for enzyme.

The concentration of each component in the reagent composition of the present invention can be varied in a wide range as follows. In the following, the concentration range of each component is a concentration range in a working solution. For example, the preferable range of cholesterol dehydrogenase is from about 0.005 to about 0.5 U/ml and that of NAD or NADP is from about 0.5 to about 20 mg/ml. The preferable concentration ranges of the cholesterol esterase, tetrazolium salt, and diaphorase all optionally usable in the present invention are from about 0.2 to about 5 U/ml, about 0.5 to about 10 mg/ml and about 0.5 to about 10 U/ml, respectively.

The preferable concentration range of surfactant and buffer is from about 10 to about 100 mg/ml surfactant and from about 10 to about 1,000 mmole/1 of a buffer solution of a pH of about 6 to about 10.

In the method for the determination of cholesterol according to the present invention, it is preferred that the detectable change be measured at least two times in a predetermined time span of about 5 minutes or less. By dividing the difference between obtained measurement values by the time difference between each measurement, the reaction rate of enzyme used can be calculated. Accordingly, no blank test is necessary.

The present invention will be explained more specifically below, by way of Preparatory Tests and Examples. The activity of the cholesterol dehydrogenase used in the Preparatory Tests and the Examples is defined according to the following measurement methods.

2.65 Ml of 0.1M tris hydrochloride buffer solution (pH 8.6), 0.1 ml of a solution containing 28 mM of NAD or NADP, 0.05 ml of a 1,4-dioxane solution containing 1 g/dl of cholesterol, and 0.05 ml of an aqueous solution containing a cholesterol dehydrogenase were mixed and incubated at 30° C. The increase of the absorbance at 340 nm of the mixture during incubation was measured. The amount of enzyme which forms 1μ mole of NADH or NADPH per minute under the above conditions has been defined as 1 unit (U).

Preparatory Test 1

Relation between Surfactant Concentration and Km Value of Cholesterol Dehydrogenase Each 1 ml of 0.1M tricin buffer solution (pH 8.5) containing 4.0, 30.0 or 100.0 mg/ml of Triton X-100, 0.01 U/ml of cholesterol dehydrgenase (manufactured by Amano Pharmaceutical Co., Ltd.), and 2.0 mg/ml of β-NAD (manufactured by Oriental Yeast Co., Ltd.),was placed in a quartz cell and kept at 30° C. Twenty μl of 1,4-dioxane solution containing 2 to 50 mg/ml of cholesterol was added to each cell and the reaction was started. The change of the absorbance at 340 nm during the reaction was measured. The measured values were subjected to plotting of Lineweaver-Burk (J. Amer, Chem. Soc., 56, 658, 1934) and the Km value of the cholesterol dehydrogenase in each reaction solution was calculated. The relation between concentration of surfactant used (Triton X-100) and Km value of cholesterol dehydrogenase used is shown in Table 1.

As is obvious from Table 1, the Km value of the cholesterol dehydrogenase increases with the increase of the concentration of Triton X-100.

TABLE 1

| Concentration of Triton X-100 (mg/ml) | Km value (mM) |
| --- | --- |
| 4.0 | 0.48 |
| 30.0 | 1.54 |
| 100.0 | 10.0 |

Preparatory Test 2

Relation between (a) Linearity of Calibration Curve for Kinetic Determination of Cholesterol and (b) Surfactant Concentration Each 1 ml of 0.1M tricin buffer solution (pH 8.5) containing 0.01 U/ml of cholesterol dehydrogenase, 2.0 mg/ml of β-NAD, and 50.0 mg/ml of Triton X-100 was placed in each of a plurality of quartz cells and kept at 30° C. Then, 20 μl of a 1,4-dioxane containing 200, 400, 600, or 800 mg/dl of cholesterol was added to each cell and the reaction was started. During the reaction, the absorbances at 340 nm of each reaction solution after 1 minute and 2 minutes from the start of the reaction were measured. The same procedure was repeated by changing the concentration of Triton X-100 to 4.0 mg/ml and 10.0 mg/ml. The increase of NADH per minute (reaction rate) was calculated by subtracting the measurement value after 2 minutes from the measurement value after 1 minute. The relation between this reaction rate and the cholesterol concentration is shown in FIG. 1. As is obvious from FIG. 1, owing to the addition of 10.0 mg/ml or 50.0 mg/ml of Triton X-100, the reaction proceeded according to the first order at least up to a cholesterol concentration of 600 mg/dl. Meanwhile, when the surfactant concentration was at a level ordinarily used, namely, 4.0 mg/ml, the linearity of the relation between the reaction rate and the cholesterol concentration was seen only up to a cholesterol concentration of 200 mg/ml.

EXAMPLE 1

Figure 2:
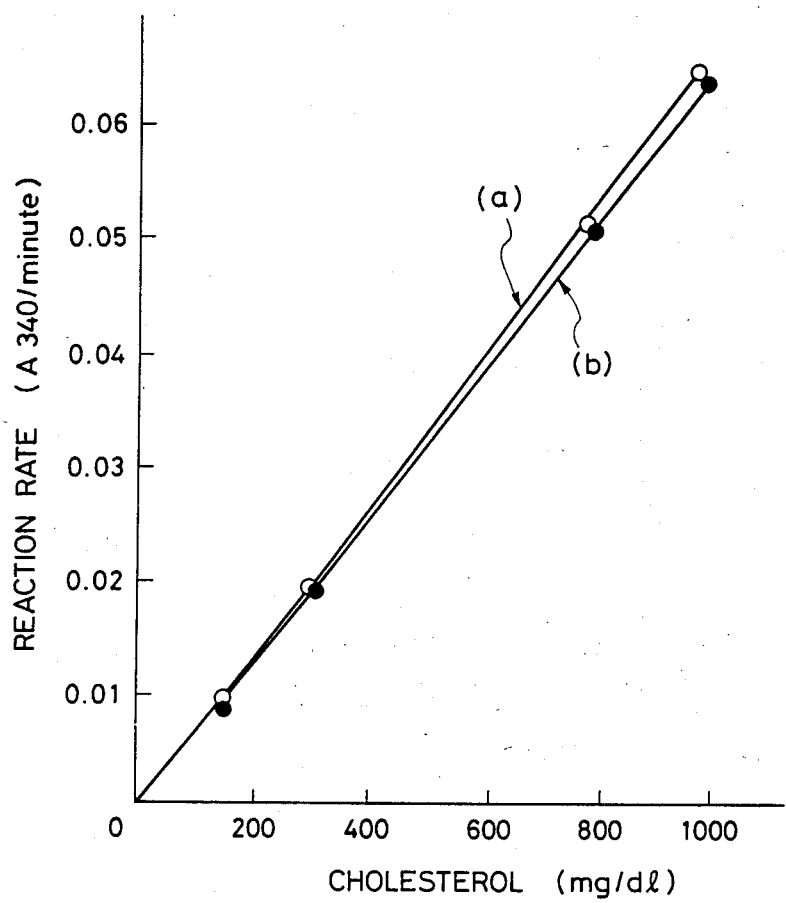
FIG. 2 illustrates the relation between cholesterol concentration in sample and formation rate of NADH (reaction rate) measured in accordance with an ultraviolet absorption method, in the method for the determination of cholesterol according to the present invention. In the graph, (a) and (b) represent cases of using, as a surfactant, Triton X-100 and Adekatol S0135, respectively.

In a quartz cell were placed (a) 1 ml of 0.1M tricin buffer solution (pH 8.5) containing 0.5 U/ml of a cholesterol esterase (manufactured by Amano Pharmaceutical Co., Ltd.), 2.0 mg/ml of β-NAD, and 50.0 mg/ml of Triton X-100 and (b) 20 μl of a serum sample containing a known concentration (150, 300, 780, or 980 mg/dl) of cholesterol. They were kept at 30° C. for 2 minutes. Then, 0.05 ml of an aqueous solution containing 1.0 U/ml of cholesterol dehydrogenase was added to each quartz cell, and the reaction was started. The absorbances at 340 nm of each reaction solution after 1 minute and 2 minutes from the start of the reaction were measured. The measurement values obtained were treated as in Preparatory Test 2 and a linearity between cholesterol concentration and reaction rate was obtained as shown in (a) of FIG. 2. As is obvious from this result, the reaction proceeded according to the first order up to a cholesterol concentration of about 1,000 mg/dl.

EXAMPLE 2

The procedure of Example 1 was repeated except that Triton X-100 used in Example 1 was replaced by Adekatol S0135. The relation between cholesterol concentration and reaction rate was linear as shown in (b) of FIG. 2. The reaction proceeded according to the first order up to a cholesterol concentration of about 1,000 mg/dl.

EXAMPLE 3

Figure 3:
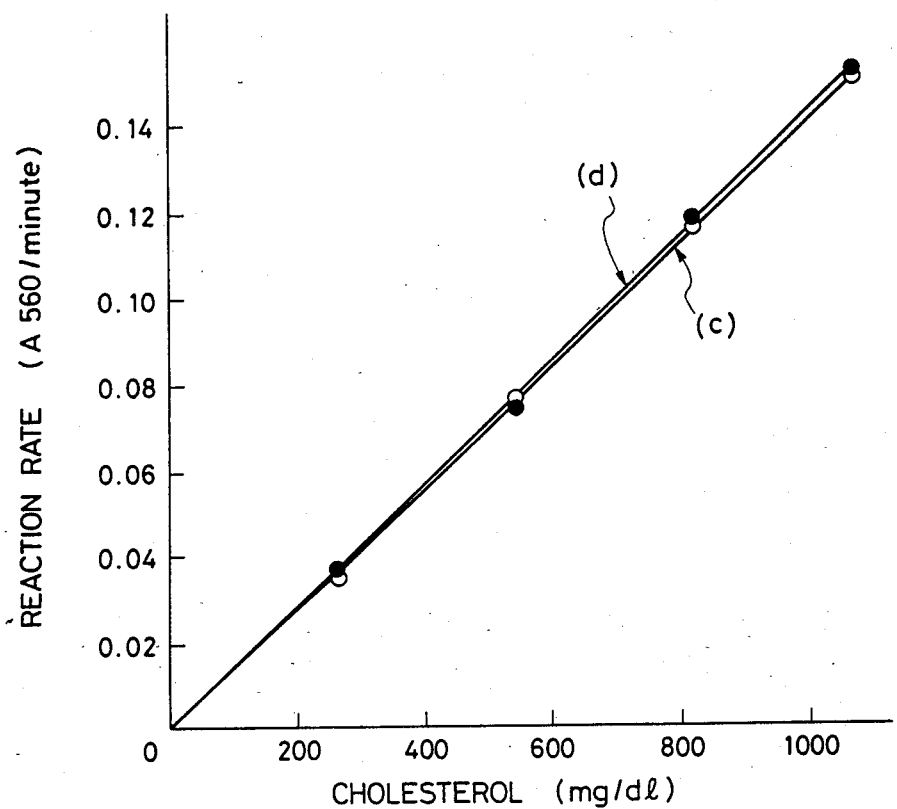
FIG. 3 illustrates the relation between cholesterol concentration in sample and formation rate of NADH (reaction rate) measured in accordance with a formazan formation method, in the method for the determination of cholesterol according to the present invention. In the graph, (c) and (d) represent cases of using, as a surfactant, Triton X-100 and Adekatol NP700, respectively.

In a quartz cell were placed (a) 1 ml of 0.1M tricin buffer solution (pH 7.5) containing 0.5 U/ml of cholesterol esterase, 1.0 U/ml of diaphorase (manufactured by Amano Pharmaceutical Co., Ltd.), 2.0 mg/ml of β-NAD, 0.01 mg/ml of Nitrotetrazolium Blue (manufactured by Dojindo Laboratories), and 20.0 mg/ml of Triton X-100 and (b) 20 μl of a serum sample containing a known concentration (274, 547, 821, or 1,095 mg/dl) of cholesterol. Each quartz cell was kept at 30° C. for 2 minutes. 0.05 ml of an aqueous solution containing 0.5 U/ml of cholesterol dehydrogenase was added to each cell, and the reaction was started. The absorbances at 560 nm of each reaction solution after 1 minute and 2 minutes from the start of the reaction were measured. The measurement values obtained were treated as in Preparatory Test 2. The relation between cholesterol concentration and reaction rate is shown by a straight line of (c) of FIG. 3, and the reaction proceeded according to the first order up to a cholesterol concentration of about 1,000 mg/dl.

EXAMPLE 4

The procedure of Example 3 was repeated except that Triton X-100 used in Example 3 was replaced by Adekatol NP 700. The relation between cholesterol concentration and reaction rate is shown by a straight line of (d) of FIG. 3. The reaction proceeded according to the first order up to a cholesterol concentration of about 1,000 mg/dl.

EXAMPLE 5

The procedures of Example 1 (measurement of absorption at ultraviolet region, of formed NADH) and Example 3 (measurement of colored substance formed) were repeated except that 10 different serum samples each containing an unknown concentration of cholesterol were used. The measurement values were compared with the calibration curves obtained in Examples 1 and 3 to determine the cholesterol concentration in each serum sample. For comparison, the same serum samples were subjected to cholesterol determination using a commercially available reagent composition for cholesterol determination containing a cholesterol oxidase [Cholesterol C Test Wako (trade name) manufactured by Wako Pure Chemical Industries, Ltd.]. All the measurement values obtained are shown in Table 2. As is obvious from Table 2, the measurement values according to the present invention agreed well with those by the known method.

TABLE 2

| Serum Sample No. | Present Invention method (Measurement of absorption at u.v. region) | Present invention method (Measurement of colored substance) | Known method |
|---|---|---|---|
| 1 | 142 mg/dl | 147 mg/dl | 145 mg/dl |
| 2 | 134 | 129 | 130 |
| 3 | 236 | 235 | 235 |
| 4 | 247 | 254 | 250 |
| 5 | 445 | 444 | 445 |
| 6 | 384 | 384 | 382 |
| 7 | 478 | 485 | 480 |
| 8 | 574 | 573 | 570 |
| 9 | 345 | 344 | 345 |
| 10 | 448 | 442 | 450 |

What is claimed is:
1. An enzymatic method for measurement of cholesterol, which comprises:
   (1) preparing a test sample;
   (2) mixing the test sample with a reagent composition comprising:
      (a) a cholesterol dehydrogenase,
      (b) an oxidizing agent selected from the group consisting of nicotinamide-adenine dinucleotide (NAD) and nicotinamide-adenine dinucleotide phosphate (NADP), and,
      (c) from about 10 to about 100 mg/ml in final working solution of non-ionic surfactant;
   (3) incubating the mixture at a room temperature from about 20° C. to about 40° C. and a pH from about 6.0 to about 10.0; and
   (4) measuring an absorbency increase per unit time of the resulting detectable oxidized and reduced products kinetically.
2. A method according to claim 1, wherein the non-ionic surfactant has a hydrophile-lipophile balance of 8 to 20.
3. A method according to claim 2, wherein the non-ionic surfactant is selected from the group consisting of polyoxyethylene alkylphenol ether polyoxyethylene alkyl ether, secondary straight alcohol ethoxylate and nonylphenol ethoxylate compounds.
4. A method according to claim 3, wherein the polyoxyethylene alkylphenol ether is selected from the group consisting of polyoxyethylene (9,10) p-t-octylphenyl ether and polyoxyethylene (8 to 85) p-nonylphenyl ether.
5. A method according to claim 3, wherein the polyoxyethylene alkyl ether is selected from the group consisting of polyoxyethylene (20) cetyl ether, polyoxyethylene (10) cetyl ether, polyoxyethylene (23) dodecyl ether, polyoxyethylene (10) lauryl ether, polyoxyethylene (14) stearyl ether, polyoxyethylene (10) oleyl ether, and polyoxyethylene (29) oleyl ether.
6. A method according to claim 1, wherein the reagent composition also contains a cholesterol esterase.
7. A method according to claim 1, wherein the reduced products are NADH or NADPH and are measured by determining the absorption by the reduced products in the ultraviolet region.
8. A method according to claim 1, wherein the reagent composition additionally contains a tetrazolium salt and diaphorase to measure the reduced products and the reduced products are NADH and NADPH.

9. A method according to claim 1, wherein the oxidized product is cholestenone and is measured by determining the absorption by the oxidized product in the ultraviolet region.

10. A method according to claim 1, wherein the cholesterol dehydrogenase is derived from a microorganism selected from the genera consisting of Nocardia, Alcaligenes, and Proteus.

11. A method according to claim 1, wherein the test sample is a human body fluid.

12. A composition for the kinetic measurement of cholesterol, comprising:
 (a) 0.005 to 0.5 U/ml of a cholesterol dehydrogenase;
 (b) 0.2 to 5 U/ml of a cholesterol esterase;
 (c) 0.5 to 20 mg/ml of nicotinamide-adenine dinucleotide or nicotinamide-adenine dinucleotide phosphate;
 (d) 10 to 100 mg/ml of a non-ionic surfactant; and
 (e) 10 to 1,000 mmol/l of a buffer solution of a pH of 6 to 10.

13. A composition for the kinetic measurement of cholesterol, comprising:
 (a) 0.005 to 0.5 U/ml of a cholesterol dehydrogenase;
 (b) 0.2 to 5 U/ml of a cholesterol esterase;
 (c) 0.5 to 10 U/ml of diaphorase;
 (d) 0.5 to 10 mg/ml of tetrazolium salt;
 (e) 0.5 to 20 mg/ml of nicotinamide-adenine dinucleotide or nicotinamide-adenine dinucleotide phosphate;
 (f) 10 to 100 mg/ml of a non-ionic surfactant; and
 (g) 10 to 1,000 mmol/l of a buffer solution of pH of 6 to 10.

* * * * *